United States Patent
Kataoka et al.

(10) Patent No.: US 6,974,856 B1
(45) Date of Patent: Dec. 13, 2005

(54) BLOCK COPOLYMERS HAVING POLYMER SEGMENT DERIVED FROM OXAZOLINE

(75) Inventors: Kazunori Kataoka, Tokyo (JP); Yukio Nagasaki, Moriya-cho (JP); Yoshitsugu Akiyama, Tokyo (JP)

(73) Assignee: Nanocarrier Co., Ltd., Chiba (JP)

( * ) Notice: Subject to any disclaimer, the term of this patent is extended or adjusted under 35 U.S.C. 154(b) by 393 days.

(21) Appl. No.: 10/048,643

(22) PCT Filed: Jun. 27, 2000

(86) PCT No.: PCT/JP00/04202

§ 371 (c)(1),
(2), (4) Date: Feb. 4, 2002

(87) PCT Pub. No.: WO01/10934

PCT Pub. Date: Feb. 15, 2001

(30) Foreign Application Priority Data

Aug. 4, 1999 (JP) .................................. 11-221026

(51) Int. Cl.$^7$ ...................... C08G 63/08; C08G 73/02; C08G 65/00; C08G 81/00
(52) U.S. Cl. ...................... 528/393; 528/373; 528/374; 528/362; 528/363; 528/403; 528/421; 528/422; 528/425; 528/10; 528/21; 525/54.2; 525/412; 525/415; 525/417; 525/437; 525/474
(58) Field of Search ........................... 528/327, 10, 21, 528/373, 374, 362, 363, 403, 421, 422, 425, 528/393; 525/54.2, 412, 415, 417, 437, 474

(56) References Cited

U.S. PATENT DOCUMENTS

| | | | |
|---|---|---|---|
| 4,644,038 A | 2/1987 | Protzman | 525/412 |
| 4,785,070 A * | 11/1988 | Rasmussen et al. | 528/73 |
| 5,183,861 A * | 2/1993 | Riffle et al. | 525/413 |
| 5,925,720 A | 7/1999 | Kataoka et al. | 525/523 |
| 5,929,177 A | 7/1999 | Kataoka et al. | 525/428 |
| 5,973,069 A | 10/1999 | Kataoka et al. | 525/54.2 |
| 6,090,317 A * | 7/2000 | Kataoka et al. | 264/4.1 |
| 6,388,041 B1 * | 5/2002 | Kataoka et al. | 528/14 |

FOREIGN PATENT DOCUMENTS

| | | |
|---|---|---|
| EP | 0 434 223 | 6/1991 |
| EP | 0 555 101 | 8/1993 |
| EP | 0 822 217 | 2/1998 |
| JP | 2-274712 | 11/1990 |
| JP | 7-300521 | 11/1995 |
| WO | 93/16687 | 9/1993 |
| WO | 99/57174 | 11/1999 |

OTHER PUBLICATIONS

Macromolecues, 199, 32, 6892-6894, "Polyion Complex Micelles with Reactive Aldehyde Groups on Their Surface from Plasm DNA and End-Functionalized Charged Block Copolymers", Kasunori Kataoka, et al , Aug. 16, 1999.*

* cited by examiner

Primary Examiner—P. Hampton Hightower
(74) Attorney, Agent, or Firm—Wenderoth, Lind & Ponack, L.L.P.

(57) ABSTRACT

Disclosed are block copolymers represented by the following general formula (I)

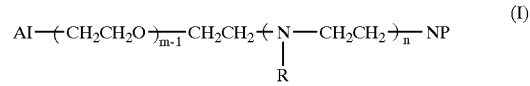

wherein AI represents a hydroxyl group or an organic residue derived from an anionic polymerization initiator, R represents a hydrogen atom or an acyl group, NP represents a residue derived from a nucleophilic reagent, m is an integer of 2 to 20,000, and n is an integer of 1 to 20,000.

9 Claims, 3 Drawing Sheets

BLOCK COPOLYMERS HAVING POLYMER SEGMENT DERIVED FROM OXAZOLINE

TECHNICAL FIELD

This invention relates to block copolymers having a polymer segment derived from oxazoline as one block. More particularly, it relates to block copolymers having a poly(ethylene oxide) segment and a polymer segment derived from oxazoline, and to a process for preparing the same.

BACKGROUND ART

It is known that poly(ethylene oxide) (hereinafter referred to as PEO) chains are highly soluble in water, are highly flexible, have extremely high motility in water, and form a hydrogel having high biocompatibility. Accordingly, in order, for example, to enhance biocompatibility, it has been proposed to graft a PEO chain to a polymers prepared from other monomers or to form a great variety of block copolymers having a PEO chain as one block.

An example of the former technique of grafting a PEO chain is found in WO 93/16687. It is claimed therein that the resulting polymers can be used for the microencapsulation of various drugs and cells.

As examples of the latter technique, block copolymers having a PEO chain as a hydrophilic domain and a poly(lactide) chain as a hydrophobic domain have been provided by some of the present inventors (see WO 96/32434, WO 96/33233 and WO 97/06202). Since these hydrophilic-hydrophobic block copolymers form a stable polymeric micelle in an aqueous medium, not only they can be used for biocompatible coating purposes, but also attention is being paid to their utilization, for example, as targeting carriers for drugs.

Meanwhile, it is proposed in recent years to use not only various modified viral vectors but also liposomes as means for internalizing genes into animal cells. It is suggested that, as typical examples of such liposomes, ones formed from cationic lipids can serve as excellent carriers for DNA.

DISCLOSURE OF THE INVENTION

The above-described graft polymers and block copolymers of the prior art each have definite excellent properties. An object of the present invention is to provide a block copolymer which, in addition to the coating properties and stable polymeric micelle-forming ability possessed by the aforesaid block copolymers, has the ability to form a coating film or polymeric micelle capable of encapsulating acidic drugs or substances (e.g., DNA and RNA) stably.

It has now been found that the above object can be accomplished by a block copolymer having a polymer segment derived from oxazoline and a PEO segment and, if necessary, having a suitable functional group at one or both of the α-end and ω-end of the polymer. Moreover, it has been recognized that the hydrophilicity/hydrophobicity balance of the polymer segment derived from oxazoline can be regulated by causing it to carry a suitable acyl group at a position corresponding to the 2-position of oxazoline and that the segment can be converted to poly(ethyleneimine) (hereinafter referred to as PEI) by eliminating the acyl group.

The present invention has been completed on the basis of these findings. Specifically, the present invention relates to a block copolymer represented by the general formula (I)

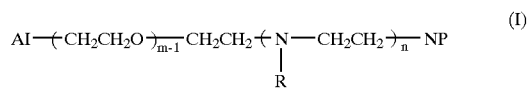

wherein AI represents a hydroxyl group or an organic residue derived from an anionic polymerization initiator, R represents a hydrogen atom or an acyl group, NP represents a residue derived from a nucleophilic reagent, m is an integer of 2 to 20,000, and n is an integer of 1 to 20,000.

Moreover, the present invention also relates to a process for the preparation of such a block copolymer.

BEST MODE OR CARRYING OUT THE INVENTION

Figure 1:
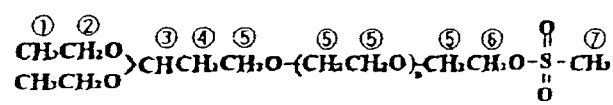
FIG. 1 is the $^1$H-NMR spectrum of PEO obtained in Example 1, and the PEO has an acetal group at one end and a mesyl group at the other end.
Figure 1:
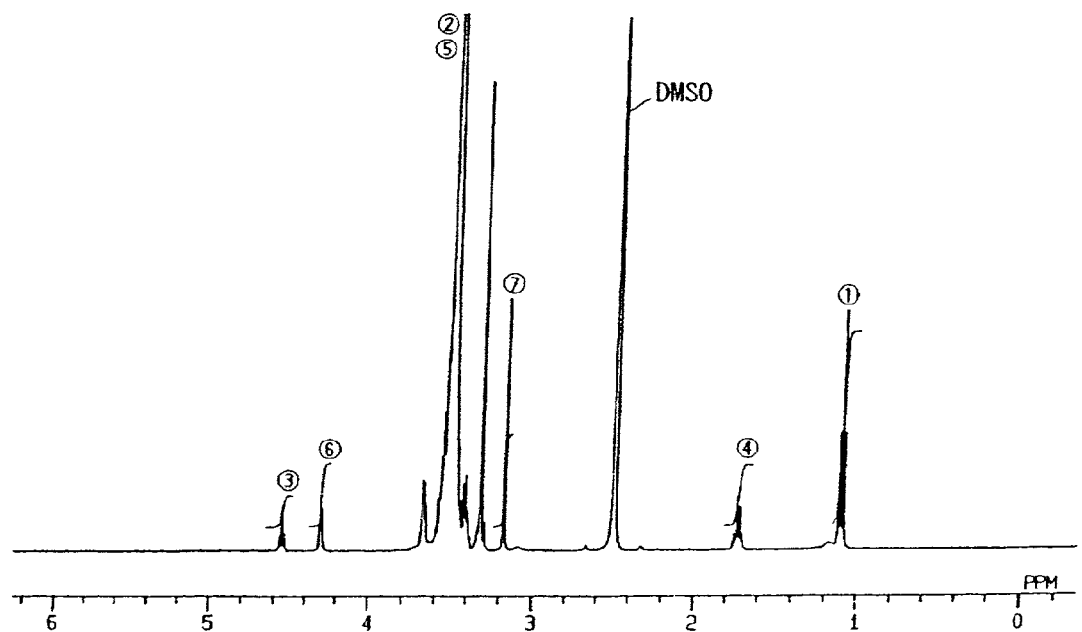

In this description, the terms having the prefix "poly" attached thereto are used as concepts which comprehend not only commonly known polymers but also oligomers.

In the general formula (I) specifying the block copolymers of the present invention, the term "organic residue derived from an anionic polymerization initiator" defining AI comprehends organic residues derived from all initiators that can be used in the polymerization of ethylene oxide. Accordingly, the PEO segment in accordance with the present invention may be a PEO segment derived from either a conventionally prepared PEO homopolymers or a precursor for the preparation thereof or a precursor PEO for the preparation of block copolymers or graft polymers containing a PEO segment.

Preferably, the PEO-containing segments which were provided by some of the present inventors and used for the preparation of block copolymers having functional groups at both ends of the polymer molecule (see WO 96/32434, WO 96/33233 and WO 97/06202, and the disclosures of these international publication pamphlets are incorporated herein by reference) may be used as PEO segments in the block copolymers of the present invention.

Specific examples of AI include, but are not limited to, groups of the following formula.

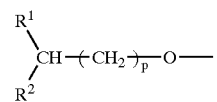

(i) In the above formula, p is an integer of 1 to 10, and $R^1$ and $R^2$ each independently represent a $C_{1-10}$ alkoxy, aryloxy or aryl-$C_{1-3}$ alkyloxy group, or $R^1$ and $R^2$ are united together to represent an optionally $C_{1-6}$ alkyl-substituted ethylenedioxy group [—O—CH(R')—CH—O—in which R' is a hydrogen atom or a $C_{1-6}$ alkyl group] or an oxy (=O) radical.

The alkyl moiety of the aforesaid alkoxy group, and the aforesaid alkyl groups may be straight-chain or branched alkyl groups. Specific examples of the alkyl moiety of the $C_{1-10}$ alkoxy group or the $C_{1-10}$ alkyl group include methyl ethyl propyl isopropyl butyl sec-butyl, tert-butyl pentyl isopentyl hexyl 2-methylpentyl, 3-methylpentyl, octyl, 2-ethylhexyl, decyl and 4-propylpentyl.

Specific examples of the $C_{1-20}$ alkyl group described later or the alkyl moiety of the $C_{2-21}$ acyl group described later include, in addition to the above-enumerated alkyl groups, 4-ethyldecyl, 8-methyldecyl, n-dodecyl n-hexadecyl and octadecyl and icosyl. These illustrations are also applied to the explanation of various groups as will be described later.

Alternatively, $R^1$ and $R^2$ may be united together to represent an optionally $C_{1-6}$ alkyl-substituted ethylenedioxy group [—O—CH(R')—CH$_2$O— in which R' is a $C_{1-6}$ alkyl group]. Preferred examples thereof include ethylenedioxy, propylenedioxy and 1,2-butylenedioxy.

When this group is hydrolyzed, $R^1$ and $R^2$ are united together to form an oxy (=O) radical. That is, this group is favorable for the preparation of the block copolymers of the present invention which have an aldehyde group at the α-end of the molecule.

Preferably, p is an integer of 1 to 5, and $R^1$ and $R^2$ each independently represent a $C_{1-6}$ alkoxy group, or $R^1$ and $R^2$ are united together to represent an optionally $C_{1-3}$ alkyl-substituted ethylenedioxy group.

(ii) Alternatively, in the above formula, p is 0 or 1, and $R^1$ and $R^2$ are united together to represent an atomic group constituting a residue derived from a monosaccharide or its derivative. Examples of the monosaccharide or its derivative include ones represented by the following formula.

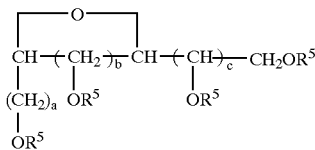

wherein one $R^5$ radical represents a chemical bond by which a covalent bond to an adjacent methylene group can be formed through the medium of an oxygen atom, and the other $R^5$ radicals each independently represent a hydrogen atom or a $C_{1-5}$ alkyl, ($C_{1-5}$ alkyl)carbonyl or tri($C_{1-5}$ alkyl) silyl group (in which these alkyl groups may be the same or different), or two $R^5$ radicals are united together to represent a $C_{3-5}$ alkylidene group that forms an acetal group together with the oxygen atoms to which they are attached, or a benzylidene group in which the methine group may be substituted by a $C_{1-3}$ alkyl group, a is 0 or an integer of 1, b is an integer of 2 or 3, and c is 0 or an integer of 1. Preferred examples of this saccharide or its derivative include natural glucose, galactose, mannose, fructose, ribose and xylose, as well as their derivatives. As specific examples of the alkyl group or alkyl moiety included in the aforesaid $C_{1-5}$ alkyl ($C_{1-5}$ alkyl)carbonyl or $C_{1-5}$ alkylsilyl group, alkyl groups having 1 to 5 carbon atoms may be selected from the alkyl groups described above in (i).

When two $R^5$ radicals are united together to represent a $C_{3-5}$ alkylidene group that forms an acetal group of the formula

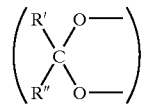

together with the oxygen atoms to which they are attached, examples of the alkylidene group include isopropylidene, 1-butylidene, 2-butylidene and 3-pentylidene. Examples of the benzylidene group in which the methine group may be substituted by a $C_{1-3}$ alkyl group include benzylidene of the formula

and methylbenzylidene of the formula

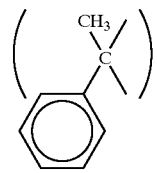

When two $R^5$ radicals form such an acetal group, this is favorable for the purpose of eliminating these $R^5$ groups selectively to obtain a saccharide residue in which each R is a hydrogen atom (i.e., having deprotected hydroxyl groups).

In the above formula, a, b and c mean 0 or certain integers which vary according to the type of the saccharide selected as the starting material. Specifically, a is 0 or 1, b is 2 or 3, and c is 0 or 1. For example, when the starting material is glucose, a is 0, b is 3, and c is 0 for D-glucopyranose that is the intramolecular hemiacetal form of glucose, or a is 0, b is 2, and c is 1 for D-glucofuranose. Accordingly, the aforesaid saccharide residue comprehends both of these forms. On the other hand, when the starting material is galactose, a is 0, b is 3, and c is 0.

(iii) Alternatively, in the above formula, p is 0 or 1, and $R^1$ and $R^2$ each independently represent a hydrogen atom, a $C_{1-20}$ alkyl group, a phenyl group, or a $C_{1-20}$ alkyl or phenyl group having one or two substituents selected from amino optionally protected by one or two amino-protecting groups, carboxyl optionally protected by a carboxyl-protecting group, and mercapto optionally protected by a mercapto-protecting group.

Specific examples of the $C_{1-10}$ alkyl and $C_{1-20}$ alkyl groups have been described above in (i).

Specific examples of the aforesaid carboxyl-protecting group include alkoxy groups of 1 to 5 carbon atoms (e.g., methoxy, ethoxy, n-propoxy, isopropoxy, n-butoxy and tert-butoxy) and phenyl-substituted methoxy groups (e.g., benzyloxy, diphenylmethoxy and triphenylmethoxy) which constitute a part of esters formed with the carboxyl group. The carboxyl group blocked by a carboxyl-protecting group also comprehends a cyano group which can form a carboxyl group under certain hydrolysis conditions.

Specific examples of the mercapto-protecting group include phenyl benzyl, trimethylsilyl acetyl o-, m- or p-methylbenzyl triethylsilyl o-, m- or p-tolyl, and tert-butyldimethylsilyl.

For further details of AI in the general formula (I) as defined above in (i) to (iii), the aforementioned WO 96/33233, WO 96/32434 and WO 97/06202 may be referred to. Moreover, the PEO segments in accordance with the present invention may be formed according to the methods for the formation of a PEO segment which are included in the processes for the preparation of block copolymers as described in these international publication pamphlets.

(iv) Moreover, specific examples of AI also include groups of the formula

wherein $R^3$ and $R^4$ each independently represent a hydrogen atom or an organosilyl type amino-protecting group, or $R^3$ and $R^4$ represent organosilyl type amino-protecting groups that, together with the nitrogen atom to which they are attached, can form a four- to seven-membered disila-azacyclo heterocyclic ring.

Specific examples of the silyl group represented by $R^3$ are groups of the formula

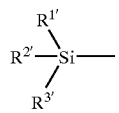

and specific examples of the silyl group represented by $R^4$ are groups of the formula

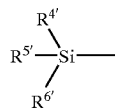

In the above formulas, $R^{1'}$, $R^{2'}$, $R^{3'}$, $R^{4'}$, $R^{5'}$ and $R^{6'}$ may each independently be an alkyl group and preferably a $C_{1-6}$ alky, group. When $R^3$ and $R^4$ are united together to form an amino-protecting group, any of $R^{1'}$, $R^{2'}$ and $R^{3'}$ may be united with any of $R^{4'}$, $R^{5'}$ and $R^{6'}$ to form a methylene, ethylene, propylene or butylene group. Specific examples of the amino-protecting group so formed include groups of the formula

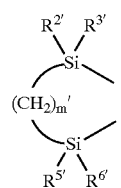

wherein m' is a positive number of 1 to 4. These groups can form four- to seven-membered disila-azacyclo heterocyclic rings together with the nitrogen atom of the amino group to which the protecting group is attached.

Among these amino-protecting groups, those which can form four- to seven-membered disila-azacyclo heterocyclic rings and in which $R^{2'}$, $R^{3'}$, $R^{5'}$ and $R^{6'}$ each independently represent a lower alkyl group are preferred. In particular, an amino-protecting group which can form 2,2,5,5-tetramethyl-2,5-disila-1-azacyclopentane is especially preferred.

AI-PEO-blocks having these AI groups may be formed by reacting ethylene oxide under per se known polymerization conditions, except that an anionic polymerization initiator of the following formula is used.

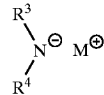

wherein $R^3$ and $R^4$ have the same meaning as defined above, except for a hydrogen atom, and M represents lithium, potassium, sodium or the like.

R in the general formula (I) represents a hydrogen atom or an acyl group. When R is a hydrogen atom, the polymer of the present invention is a PEO-poly(ethyleneimino) block copolymer. In addition to a carbonyl group, the acyl group may contain a $C_{1-20}$ alkyl group, a $C_{6-10}$ carbocyclic aromatic group which may be substituted by one or more like or different $C_{1-6}$ alkyl groups or halogen atoms, or a $C_{1-6}$ perfluoroalkyl group. When the alkyl moiety of the acyl group is a $C_{1-20}$ alkyl group, specific examples of the $C_{1-20}$ alkyl group have been described previously in (i). Examples of the aforesaid $C_{6-10}$ carbocyclic aromatic group which may be substituted include phenyl, p-methylphenyl, p-chlorophenyl and β-naphthyl. Examples of the $C_{1-6}$ perfluoroalkyl group include the above-described $C_{1-6}$alkyl groups in which two or more hydrogen atoms have been replaced by fluorine atoms, such as trifluoromethyl. By choosing the chain length or type of the acyl group represented by R, the hydrophilicity/hydrophobicity of the domain represented by the formula

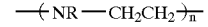

can be regulated.

NP in the general formula (I) represents a residue derived from a nucleophilic reagent (or anionoid reagent), and there may be used any such group that is fit for the purpose of the present invention. Specific examples thereof include —OH, —SH, —CN, —NH$_2$, —COOH, —OCOC(CH$_3$)=CH$_2$,

—OCH$_2$CH=CH$_2$ and —CH$_2$CH$_2$CH$_2$Si(OR") (in which R" is a $C_{1-6}$alkyl group).

No particular limitation is placed on the values of m and n in the general formula (I), provided that the block copolymer represented by this general formula has film-forming properties or polymeric micelle-forming properties. Generally, m is an integer of 2 to 20,000 and n is an integer of 1 to 20,000. Preferably, m is an integer of 10 to 10,000 and more preferably 10 to 4,000, and n is an integer of 10 to 5,000 and more preferably 10 to 500.

The block copolymers of the general formula (1) may be prepared by employing a combination of per se known reactions according to the following reaction scheme.

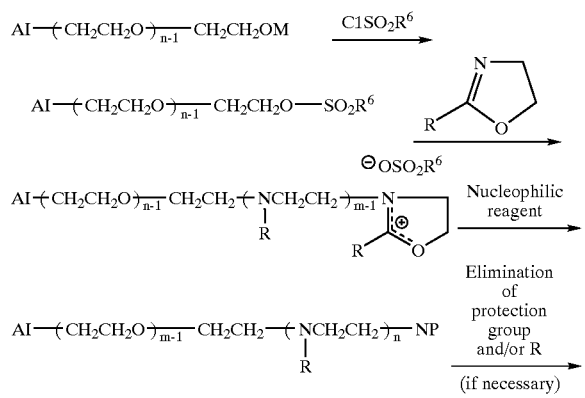

The aforesaid block copolymers in accordance with the present invention are novel compounds and may be more efficiently prepared by the following process in accordance with another embodiment of the present invention.

Specifically, the present invention also relates to a process for the preparation of a block copolymer represented by the general formula (I)

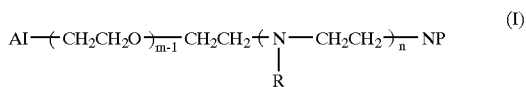

(I)

wherein AI represents a hydroxyl group or an organic residue derived from an anionic polymerization initiator, R represents a hydrogen atom or a $C_{2-21}$ acyl group, NP represents a residue derived from a nucleophilic reagent, m is an integer of 2 to 20,000, and n is an integer of 1 to 20,000, the process comprising the steps of reacting a polyethylene oxide derivative of the general formula (I-a)

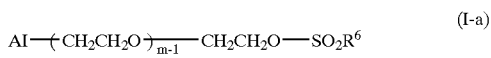

(I-a)

wherein AI and m have the same meanings as defined above, and $R^6$ represents a $C_{1-6}$ alkyl group, an optionally $C_{1-6}$ alkyl-substituted phenyl group, or a $C_{1-6}$ perfluoroalkyl group, with an oxazoline derivative of the general formula (I-b)

(I-b)

wherein $R_b$ represents a hydrogen atom or a $C_{1-20}$ alkyl group, a $C_{6-10}$ carbocyclic aromatic group which may be substituted by one or more like or different $C_{1-6}$ alkyl groups or halogen atoms, or a $C_{1-6}$ perfluoroalkyl group, in an inert solvent; reacting the resulting polymer with a nucleophilic reagent; and eliminating the acyl group, if necessary.

Although specific examples of the various groups represented by $R^6$ in the general formula (I-a) may be those described above, $R^6$ is preferably methyl. Moreover, the optionally $C_{1-6}$ alkyl-substituted phenyl group is preferably a p-methyl-substituted phenyl group.

Although the inert solvent used for the aforesaid reaction may be an aprotic polar solvent, nitromethane is preferred. It is desirable to carry out the reaction under an atmosphere of an inert gas such as argon. The proportion of the oxazoline derivative of formula (I-b) to the macromer of formula (I-a) may be chosen according to the chain length (i.e., the value of n) of the segment of the formula $$-(NR-CH_2CH_2)_n-$$

Theoretically, the value of n can be increased to a desired extent by increasing the proportion of the oxazoline derivative of formula (I-b). Most of the oxazoline derivative represented by formula (I-b) are well known as monomers for polymerization use. Even in case of novel derivatives, they may be prepared in substantially the same manner as well-known derivatives. The concentrations of these reactants in the reaction mixture are not limited, so long as the reaction mixture can be stirred. However, those skilled in the art will be able to conduct a small-scale experiment and thereby determine the optimum conditions easily according to the properties of the desired block copolymer.

Any reaction temperature may be used, so long as the desired polymerization reaction is not adversely affected. However, the reaction is usually carried out at a temperature of 30 to 100° C. The reaction time cannot be specified because the optimum time varies with the desired value of n, the reaction temperature, or the oxazoline derivative used. However, the reaction is usually carried out for 1 to 200 hours.

The polymer thus obtained may be reacted with a nucleophilic reagent to introduce a residue derived from the nucleophilic reagent at one end of the polymer. When the block copolymer obtained by reaction with a nucleophilic reagent has a hydroxyl group at ω-end, the hydroxyl group may be converted to another functional group according to the method described in the aforementioned WO 96/32434, WO 96/33233 or WO 97/06202. Moreover, when R is an acyl group and AI has a functional group protected by some protecting group, the block copolymer obtained in the above-described manner may be subjected to a reaction for eliminating the acyl group or the protecting group, if necessary.

Thus, the present invention can provide block copolymers represented by the general formula (I). These polymers can be used for various coating purposes. Moreover, they can form a stable polymeric micelle in an aqueous medium and, therefore, are useful as carriers for drugs such as DNA and RNA.

Now, among the block copolymers represented by the general formula (I), block copolymers in which AI is represented by the formula

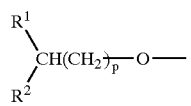

and R[1], R[2] and p are defined in (i) will be specifically explained below in the main. However, it is to be understood that the present invention can provide block copolymers having other AI groups and such substances are also fit for the purpose of the present invention.

EXAMPLE 1

Synthesis of an Acetal-PEO-MS (Macromer)

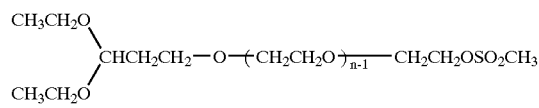

Under an atmosphere of argon at room temperature, 30 ml of tetrahydrofuran (THF), 2 mmol of 3,3-diethoxy-1-propanol as an initiator, and 2 mmol of potassium naphthalene were placed in an eggplant type flask, and stirred for 10 minutes to effect metallization. Then, 120 mmol of ethylene oxide was added thereto and polymerized by stirring at room temperature for 2 days. Using an isobaric dropping funnel, the resulting polymerization mixture containing PEO was added to a separately prepared 5 ml of a THE solution containing 40 mmol of methylsulfonyl chloride, followed by carrying out a termination reaction for 2 days.

Thereafter, the polymer was extracted with chloroform, and the extract was washed with a saturated aqueous solution of sodium chloride and dehydrated with anhydrous $Na_2SO_4$. Then, the polymer was purified by reprecipitation with diethyl ether. After vacuum drying, the polymer was analyzed by $^1$H-NMR spectroscopy (DMSO, 400 MHz). The $^1$H-NMR spectrum so recorded is shown in FIG. 1. It can be seen from this spectrum that the macromer thus obtained is PEO having an acetal group at one end and a sulfonyl group at the other end.

EXAMPLE 2

Cationic Polymerization of 2-methyl-2-oxazoline from the Macromer

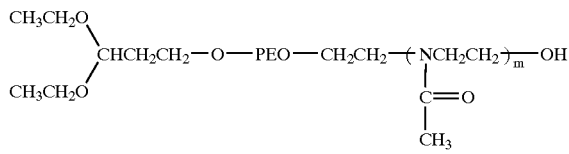

Figure 2:
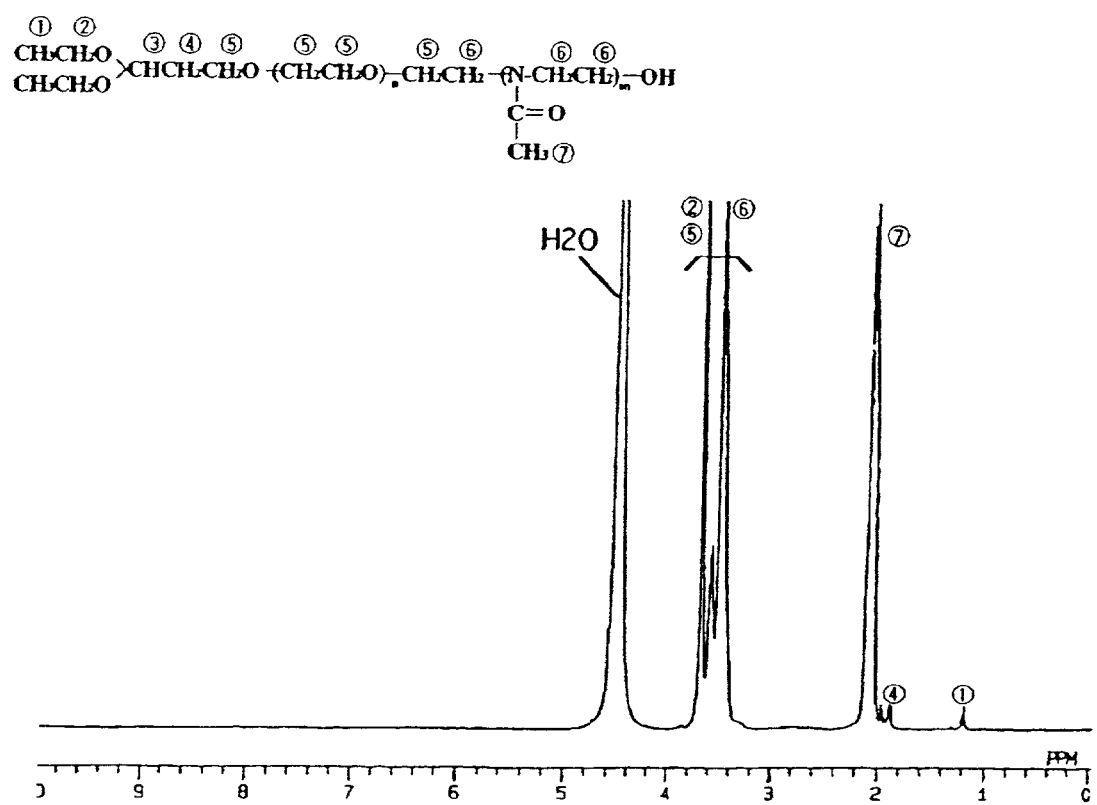
FIG. 2 is the $^1$H-NMR spectrum of the PEO-poly(2-acetyl-2-oxazoline) block copolymer obtained in Example 2.

Under an atmosphere of argon, 10 ml of nitromethane was added to 1.065 g of the vacuum-dried macromer of Example 1 (Mn= 2,700) ([macromer]O=0.0394 mol/l in $CH_3NO_2$), followed by stirring. Then, 1 ml of dodecane was added thereto as an internal standard substance. Moreover, 3.10 ml (charged so as to give a molecular weight of 10,000 and a [2-methyl-2-oxazoline]O/[macromer]O ratio of 86) of 2-methyl-2-oxazoline was added thereto and reacted at 60° C. After completion of the reaction, the polymer was extracted with chloroform, and the extract was washed with a saturated aqueous solution of sodium chloride and dehydrated with anhydrous $Na_2SO_4$. Then, the polymer was purified by reprecipitation with diethyl ether. After vacuum drying, the polymer was analyzed by $^1$H-NMR spectroscopy (DMSO, 400 MHz). The $^1$H-NMR spectrum so recorded is shown in FIG. 2.

EXAMPLE 3

Hydrolysis of the acetal-PEO-poly(2-methyl-2-oxazoline) Block Copolymer

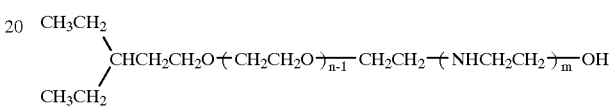

Figure 3:
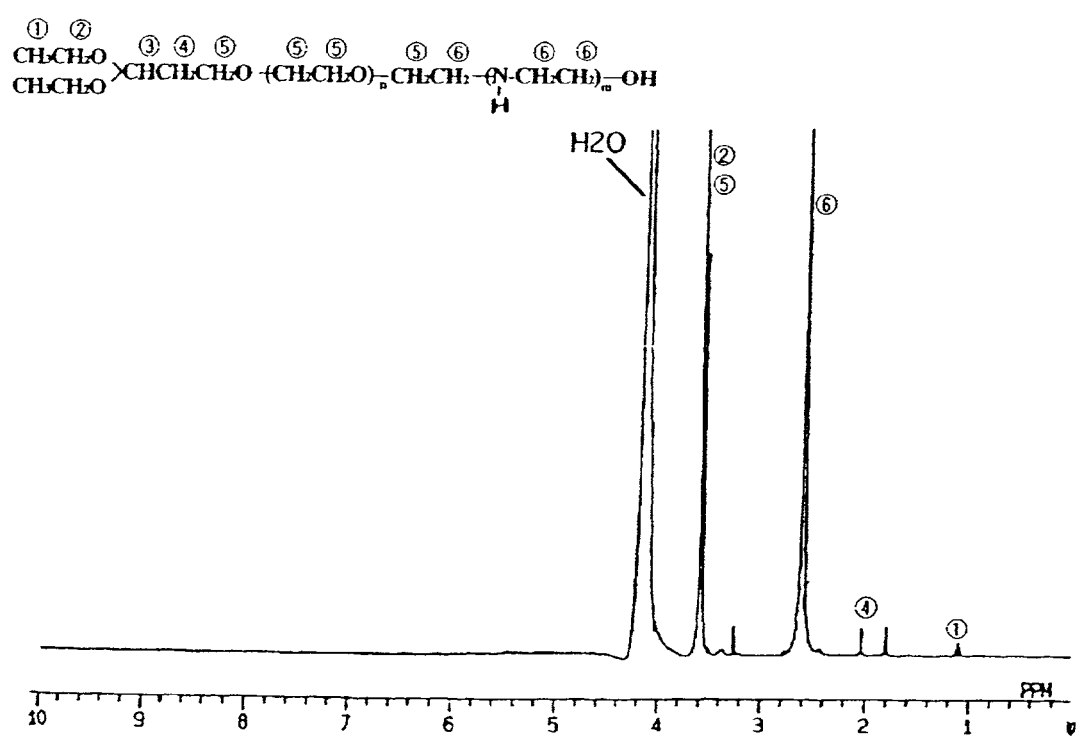
FIG. 3 is the $^1$H-NMR spectrum of the PEO-PEI block copolymer obtained in Example 3.

1.0 g (corresponding to 9.41 mmol of N-acetyl group) of the block copolymer having a poly(2-methyl-2-oxazoline) segment as obtained in Example 2 was dissolved in 10 ml of a solvent mixture composed of methanol and ethylene glycol (1:1), and reacted at 95° C. for 4 hours. Thereafter, the product was desalted and purified by dialysis, freeze-dried, and analyzed by $^1$H-NMR spectroscopy (DMSO, 400 MHz). The $^1$H-NMR spectrum so recorded is shown in FIG. 3.

EXAMPLE 4 (FOR REFERENCE)

Synthesis of a Monosaccharide Derivative-PEO

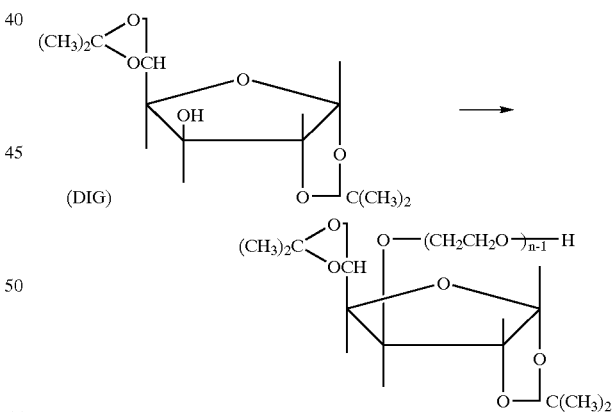

260 mg of DIG, 20 ml of THF, and 2 ml of a 0.5 mol/L tetrahydrofuran solution of potassium naphthalene were placed in a reaction vessel, and stirred for 3 minutes under an atmosphere of argon to form 3-O-potassium-1,2:5,6-di-O-isopropylidene-D-glucofuranose. Then, 5.7 g of ethylene oxide was added to this solution and stirred at room temperature under a pressure of one atmosphere. After two days of reaction, the reaction was stopped by the addition of a small amount of water. Then, the reaction mixture was poured into ether to precipitate the polymer so formed. The resulting precipitate was purified by freeze-drying from benzene. Its yield was 5.6 g (94%). The polymer obtained by gel permeation chromatography had a single peak, and its number-average molecular weight was 2,500.

EXAMPLE 5 (FOR REFERENCE)

Synthesis of an alkyl-PEO having an Amino Substituent Protected by an Amino-Protecting Group

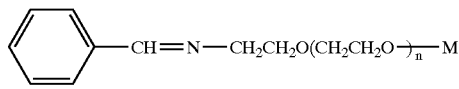

20 ml of THF, 0.15 g of 2-benzaliminoethanol, and 2 ml of a 0.5 mol/L THF solution of potassium naphthalene were placed in a reaction vessel and stirred for 3 minutes under an atmosphere of argon to form the reaction product of 2-benzaliminoethanol with potassium (potassium 2-benzaliminoethoxide).

Then, 8.8 g of ethylene oxide was added to this solution and stirred at room temperature under a pressure of one atmosphere. After two days of reaction, a polymer having about 9,000 PEO units was obtained.

EXAMPLE 6

Synthesis of a Polyoxyethylene Derivative having a Silyl-Protected Amino Group at one End

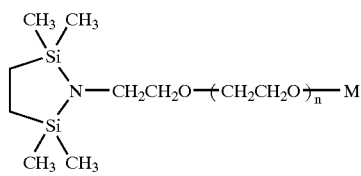

In an eggplant type flask under an atmosphere of argon, 1 mmol of 2,2,5,5-tetramethyl-2,5-disila-1-azacyclopentane and 1 mmol of potassium naphthalene were added to 50 ml of THF. Thus, there was formed a potassium amide serving as an initiator. Then, 100 mmol of ethylene oxide was added thereto and reacted at room temperature for 2 days to obtain the title derivative.

Block copolymers in accordance with the present invention can be synthesized by subjecting each of the PEO derivatives obtained in the foregoing Examples 4–6 to sulfonylation according to the procedure of Example 1; cationic polymerization according to the procedure of Example 2; and, if necessary, hydrolysis according to the procedure of Example 3.

Industrial Applicability

The present invention provides block copolymers containing a hydrophilic segment having any of various functional groups at one end and a poly(ethyleneimine) segment which may have an acyl group attached to the N atom, as well as a process for the preparation of such block copolymers. These block copolymers not only have excellent coating properties and a stable polymeric micelle-forming ability, but also have the ability to encapsulate acidic drugs (e.g., DNA and RNA) stably in such polymeric micelle. Accordingly, the present invention can be utilized, for example, in the manufacture of medical appliances to which a biocompatible coating is applied, in the manufacture of pharmaceutical preparations for achieving the targeting delivery of drugs, and in the manufacture of polymeric materials.

What is claimed is:

1. A block copolymer represented by the general formula (I)

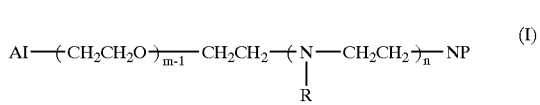

wherein AI represents a hydroxyl group or a group of the formula

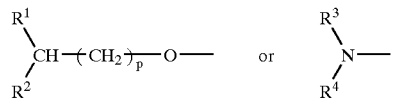

wherein (i) p is an integer of 1 to 10, and $R^1$ and $R^2$ each independently represent a $C_{1-10}$ alkoxy, aryloxy or aryl-$C_{1-3}$ alkyloxy group, or $R^1$ and $R^2$ are united together to represent an optionally $C_{1-6}$ alkyl-substituted ethylenedioxy group [—O—CH(R')—CH—O— in which R' is a hydrogen atom or a $C_{1-6}$ alkyl group] or an oxy (=O) radical; or (ii) p is 0 or 1, and $R^1$ and $R^2$ are united together to represent an atomic group constituting a residue derived from a monosaccharide or its derivative; or (iii) p is 0 or 1, and $R^1$ and $R^2$ each independently represent a hydrogen atom, a $C_{1-20}$ alkyl group, a phenyl group, or a $C_{1-20}$ alkyl or phenyl group having one or two substituents selected from amino optionally protected by one or two amino-protecting groups, carboxyl optionally protected by a carboxyl-protecting group, and mercapto optionally protected by a mercapto-protecting group; and (iv) $R^3$ and $R^4$ each independently represent a hydrogen atom or an organosilyl amino-protecting group, or $R^3$ and $R^4$ represent organosilyl amino-protecting groups that, together with the nitrogen atom to which they are attached, can form a four- to seven-membered disilaazacyclo heterocyclic ring, R represents a hydrogen atom, NP represents a residue derived from a nucleophilic reagent, m is an integer of 2 to 20,000, and n is an integer of 1 to 20,000.

2. A block copolymer as claimed in claim 1 wherein AI in the general formula (I) represents a hydroxyl group or a group of the formula

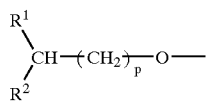

wherein p is an integer of 1 to 5, and $R^1$ and $R^2$ each independently represent a $C_{1-6}$ alkoxy group, or $R^1$ and $R^2$ are united together to represent an optionally $C_{1-3}$ alkyl-substituted ethylenedioxy group.

3. A block copolymer as claimed in claim 1 wherein AI in the general formula (I) represents a group of the formula

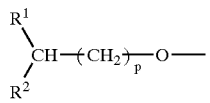

wherein p is 0 or 1, and $R^1$ and $R^2$ are united together to represent an atomic group constituting a residue derived from a monosaccharide or its derivative, and the monosaccharide or its derivative is represented by the formula

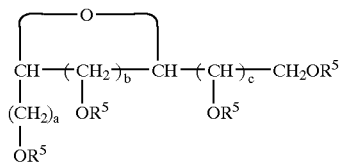

wherein one $R^5$ radical represents a chemical bond by which a covalent bond to an adjacent methylene group can be formed through the medium of an oxygen atom, and the other $R^5$ radicals each independently represent a hydrogen atom or a $C_{1-5}$ alkyl, ($C_{1-5}$ alkyl)carbonyl or tri($C_{1-5}$ alkyl) silyl group (in which these alkyl groups may be the same or different), or two $R^5$ radicals are united together to represent a $C_{3-5}$ alkylidene group that forms an acetal group together with the oxygen atoms to which they are attached, or a benzylidene group in which the methine group may be substituted by a $C_{1-3}$ alkyl group, a is 0 or an integer of 1, b is an integer of 2 or 3, and c is 0 or an integer of 1.

4. A block copolymer as claimed in claim 1 wherein AI in the general formula (I) represents a group of the formula

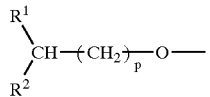

wherein p is 0 or 1, and $R^1$ and $R^2$ each independently represent a hydrogen atom, a $C_{1-20}$ alkyl group, a phenyl group, or a $C_{1-6}$ alkyl or phenyl group having a substituent selected from amino, carboxyl and mercapto.

5. A block copolymer as claimed in claim 1 wherein AI in the general formula (I) represents a group of the formula

wherein $R^3$ and $R^4$ represent organosilyl amino-protecting groups that, together with the nitrogen atom to which they are attached, can form a four- to seven-membered disila-azacyclo heterocyclic ring.

6. A block copolymer as claimed in claim 1 wherein NP in the general formula (I) is —OH, —SH, —CN, —NH$_2$, —COOH, —OCOC(CH$_3$)=CH$_2$,

—OCH$_2$CH=CH$_2$ or —CH$_2$CH$_2$CH$_2$Si(OR") (in which R" is a $C_{1-6}$ alkyl group).

7. A block copolymer as claimed in claim 1 wherein AI in the general formula (I) represents a hydroxyl group or a group of the formula

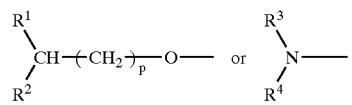

wherein
(i) p is an integer of 1 to 10, and $R^1$ and $R^2$ each independently represent a $C_{1-10}$ alkoxy aryloxy or aryl-$C_{1-3}$ alkyloxy group, or $R^1$ and $R^2$ are united together to represent an optionally $C_{1-6}$ alkyl-substituted ethylenedioxy group [—O—CH(R')—CH—O— in which R' is a hydrogen atom or a $C_{1-6}$ alkyl group] or an oxy (=O) radical; or
(ii) p is 0 or 1, and $R^1$ and $R^2$ are united together to represent an atomic group constituting a residue derived from a monosaccharide or its derivative; or
(iii) p is 0 or 1, and $R^1$ and $R^2$ each independently represent a hydrogen atom, a $C_{1-20}$ alkyl group, a phenyl group, or a $C_{1-20}$ alkyl or phenyl group having one or two substituents selected from amino optionally protected by one or two amino-protecting groups, carboxyl optionally protected by a carboxyl-protecting group, and mercapto optionally protected by a mercapto-protecting group; and
(iv) $R^3$ and $R^4$ each independently represent a hydrogen atom or an organosilyl amino-protecting group, or $R^3$ and $R^4$ represent organosilyl amino-protecting groups that, together with the nitrogen atom to which they are attached, can form a four- to seven-membered disila-azacyclo heterocyclic ring; and NP is —OH, —SH, —CN, —NH$_2$, —COOH, —OCOC(CH$_3$)=CH$_2$,

—OCH$_2$CH=CH$_2$ or —CH$_2$CH$_2$CH$_2$Si(OR″) (in which R″ is a C$_{1-6}$ alkyl group).

8. A block copolymer as claimed in claim 1 wherein AI in the general formula (I) represents a hydroxyl group or a group of the formula

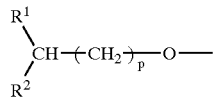

wherein p is an integer of 1 to 5, and R$^1$ and R$^2$ each independently represent a C$_{1-6}$ alkoxy group, or R$^1$ and R$^2$ are united together to represent an optionally C$_{1-3}$ alkyl-substituted ethylenedioxy group; and NP is OH.

9. A process for the preparation of a block copolymer represented by the general formula (I)

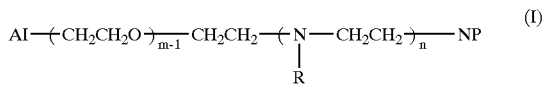

wherein AI represents a hydroxyl group or a group of the formula

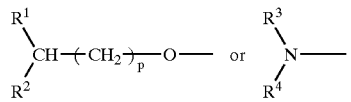

wherein
(i) p is an integer of 1 to 10, and R$^1$ and R$^2$ each independently represent a C$_{1-10}$ alkoxy, aryloxy or aryl-C$_{1-3}$ alkyloxy group, or R$^1$ and R$^2$ are united together to represent an optionally C$_{1-6}$ alkyl-substituted ethylenedioxy group [—O—CH(R′)—CH—O— in which R′ is a hydrogen atom or a C$_{1-6}$ alkyl group] or an oxy (=O) radical; or
(ii) p is 0 or 1, and R$^1$ and R$^2$ are united together to represent an atomic group constituting a residue derived from a monosaccharide or its derivative; or
(iii) p is 0 or 1, and R$^1$ and R$^2$ each independently represent a hydrogen atom, a C$_{1-20}$ alkyl group, a phenyl group, or a C$_{1-20}$ alkyl or phenyl group having one or two substituents selected from amino optionally protected by one or two amino-protecting groups, carboxyl optionally protected by a carboxyl-protecting group, and mercapto optionally protected by a mercapto-protecting group; and
(iv) R$^3$ and R$^4$ each independently represent a hydrogen atom or an organosilyl amino-protecting group, or R$^3$ and R$^4$ represent organosilyl amino-protecting groups that, together with the nitrogen atom to which they are attached, can form a four- to seven-membered disila-azacyclo heterocyclic ring, R represents a hydrogen atom, NP represents a residue derived from a nucleophilic reagent, m is an integer of 2 to 20,000, and n is an integer of 1 to 20,000, the process comprising reacting a polyethylene oxide derivative of the general formula (I-a)

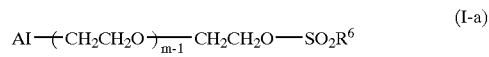

wherein AI and m have the same meanings as defined above, and R$^6$ represents a C$_{1-6}$ alkyl group, an optionally C$_{1-6}$ alkyl-substituted phenyl group, or a C$_{1-6}$ perfluoroalkyl group, with an oxazoline derivative of the general formula (I-b)

wherein R$_b$ represents a hydrogen atom or a C$_{1-20}$ alkyl group, a C$_{6-10}$ carbocyclic aromatic group which may be substituted by one or more like or different C$_{1-6}$ alkyl groups or halogen atoms, or a C$_{1-6}$ perfluoroalkyl group, in an inert solvent; reacting the resulting polymer with a nucleophilic reagent; and eliminating the acyl group, if necessary, and a protecting group or groups in AI, if present.

* * * * *